United States Patent
Suzuki

(10) Patent No.: US 9,933,371 B2
(45) Date of Patent: Apr. 3, 2018

(54) VISUAL INSPECTION APPARATUS AND VISUAL INSPECTION METHOD

(71) Applicant: YAMAHA HATSUDOKI KABUSHIKI KAISHA, Shizuoka-ken (JP)

(72) Inventor: Yoshikuni Suzuki, Shizuoka (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 34 days.

(21) Appl. No.: 15/103,428

(22) PCT Filed: Jan. 8, 2014

(86) PCT No.: PCT/JP2014/050109
§ 371 (c)(1),
(2) Date: Jun. 10, 2016

(87) PCT Pub. No.: WO2015/104799
PCT Pub. Date: Jul. 16, 2015

(65) Prior Publication Data
US 2016/0320314 A1    Nov. 3, 2016

(51) Int. Cl.
*G01B 11/30* (2006.01)
*G01N 21/95* (2006.01)
(Continued)

(52) U.S. Cl.
CPC .............. *G01N 21/95* (2013.01); *B23K 1/00* (2013.01); *B23K 1/0016* (2013.01);
(Continued)

(58) Field of Classification Search
CPC ................................ G01B 11/30; G01B 11/24
(Continued)

(56) References Cited

U.S. PATENT DOCUMENTS 5,064,291 A * 11/1991 Reiser .............. G01N 21/95684
348/131
5,166,985 A * 11/1992 Takagi ............... G01N 21/8806
348/128
(Continued)

FOREIGN PATENT DOCUMENTS

JP    03-072204 A    3/1991
JP    2004-172464 A    6/2004
(Continued)

OTHER PUBLICATIONS

The extended European search report issued by the European Patent Office dated Dec. 1, 2016, which corresponds to European Patent Application No. 14878058.8-1702 and is related to U.S. Appl. No. 15/103,428.
(Continued)

*Primary Examiner* — Roy M Punnoose
(74) *Attorney, Agent, or Firm* — Studebaker & Brackett PC

(57) ABSTRACT

A visual inspection apparatus and a visual inspection method enabling the quality of a state of solder to be properly judged. Specifically, in the visual inspection apparatus and visual inspection method, a slope (concave slope region) present on a surface of solder is searched and the quality of a state of the solder is judged based on that result. The quality of the state of the solder can be properly judged based on not a height of the solder, but the slope of the surface of the solder.

10 Claims, 7 Drawing Sheets

(51) Int. Cl.
  *G01N 21/956* (2006.01)
  *B23K 31/12* (2006.01)
  *G01B 11/25* (2006.01)
  *B23K 1/00* (2006.01)
  *H05K 3/34* (2006.01)
  *B23K 101/42* (2006.01)

(52) U.S. Cl.
  CPC ........ *B23K 31/125* (2013.01); *G01B 11/2531* (2013.01); *G01N 21/956* (2013.01); *B23K 2201/42* (2013.01); *H05K 3/3442* (2013.01); *H05K 2203/163* (2013.01)

(58) Field of Classification Search
  USPC .................................................. 356/601, 612
  See application file for complete search history.

(56) References Cited

U.S. PATENT DOCUMENTS

| | | | | |
|---|---|---|---|---|
| 5,245,671 | A * | 9/1993 | Kobayashi | G01N 21/8806 356/237.5 |
| 5,267,217 | A * | 11/1993 | Tokura | G01B 11/24 356/237.1 |
| 5,293,324 | A * | 3/1994 | Tokura | G01N 21/95684 382/141 |
| 6,023,663 | A * | 2/2000 | Kim | G01N 21/95684 382/150 |
| 6,111,602 | A * | 8/2000 | Kim | G01N 21/95684 348/92 |
| 6,421,629 | B1 * | 7/2002 | Ishiyama | G01B 11/255 702/159 |
| 6,870,611 | B2 * | 3/2005 | Savareigo | G01N 21/95684 356/237.1 |
| 6,947,151 | B2 * | 9/2005 | Fujii | G01N 21/8806 356/237.1 |
| 7,171,037 | B2 * | 1/2007 | Mahon | G01N 21/95684 382/145 |
| 7,352,892 | B2 * | 4/2008 | Zhang | G06T 7/586 345/419 |
| 7,394,084 | B2 * | 7/2008 | Kuriyama | G01N 21/8806 250/559.34 |
| 7,505,149 | B2 * | 3/2009 | Ishiba | G01N 21/95684 356/237.1 |
| 9,091,668 | B2 * | 7/2015 | Hong | G01N 21/956 |
| 9,116,504 | B2 * | 8/2015 | Kurashige | G01B 11/25 |
| 9,221,128 | B2 * | 12/2015 | Jeong | B23K 31/125 |
| 2004/0220770 | A1 * | 11/2004 | Isumi | G06T 7/0008 702/179 |
| 2013/0076857 | A1 * | 3/2013 | Kurashige | G01B 11/25 348/40 |

FOREIGN PATENT DOCUMENTS

| | | |
|---|---|---|
| JP | 2005-274558 A | 10/2005 |
| JP | 2008-122361 A | 5/2008 |
| JP | 2010-071844 A | 4/2010 |
| JP | 2013-148361 A | 8/2013 |
| KR | 10-2013-0084617 A | 7/2013 |

OTHER PUBLICATIONS

International Search Report issued in PCT/JP2014/050109; dated Apr. 15, 2014.

* cited by examiner

F I G. 9
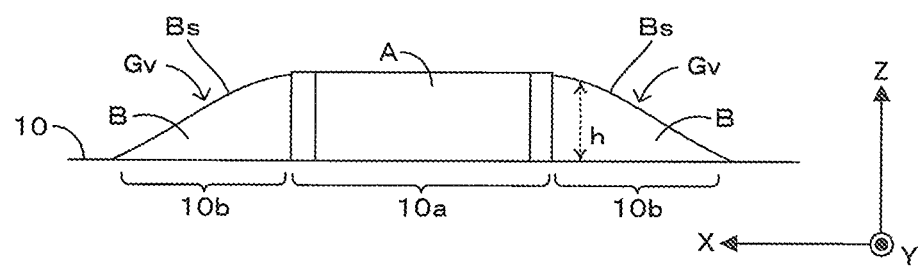

VISUAL INSPECTION APPARATUS AND VISUAL INSPECTION METHOD

CROSS REFERENCE TO RELATED APPLICATIONS

This application claims benefit of priority to International Patent Application No. PCT/JP2014/050109 filed Jan. 8, 2014, the entire content of which is incorporated herein by reference.

TECHNICAL FIELD

This disclosure relates to a visual inspection apparatus and a visual inspection method for inspecting the appearance of solder.

BACKGROUND

A technology for measuring a three-dimensional shape of an object is proposed in JP2010-071844A and JP2008-122361A. Particularly, a board visual inspection apparatus of JP2010-071844A measures a height of the fillet of solder joining a component to a board. Specifically, this board visual inspection apparatus irradiates a plurality of rays of light having mutually different colors to the solder from different directions and images the solder by a camera arranged above the solder. An approximate curve representing a change of an inclination angle of a surface of the solder is set based on the color of each region of the surface of the solder imaged in an imaging result, and the height of the solder is specified by integrating this approximation curve. The height of the solder specified in this way is used as a reference for judging the quality of a state of the solder.

SUMMARY

Technical Problem

However, in the method using the height of the solder as a reference, there has been a possibility that the quality of the state of the solder cannot be properly judged. For example, if the component repels the solder due to poor wettability of the solder, the solder can have such a defective shape that the amount of the solder is small near the component and, on the other hand, the solder rises at a distance from the component. Such a defective shape has a certain height at a position distant from the component. Thus, in the method using the height of the solder as a reference, there has been a possibility that the state of the solder having such a defective shape is erroneously judged to be good.

This disclosure was developed in view of the above problem and aims to provide a visual inspection apparatus and a visual inspection method enabling the quality of a state of solder to be properly judged.

Solution to Problem

To achieve the aim, the visual inspection apparatus according to the present disclosure, comprises: a measurement unit that measures a three-dimensional shape of a surface of solder joining a component to a board; and a control unit that searches a slope present on the surface of the solder based on a measurement result of the three-dimensional shape; wherein the control unit judges the quality of a state of the solder based on a result of searching the slope.

To achieve the aim, the visual inspection method according to the present disclosure, comprises: a step of measuring a three-dimensional shape of a surface of solder joining a component to a board; a step of searching a slope present on the surface of the solder based on a measurement result of the three-dimensional shape; and a step of judging the quality of a state of the solder based on a result of searching the slope.

In the thus configured disclosure (visual inspection apparatus, visual inspection method), the slope present on the surface of the solder is searched and the quality of the state of the solder is judged based on that result. The quality of the state of the solder can be properly judged based on not a height of the solder, but the slope of the surface of the solder in this way.

On this occasion, the visual inspection apparatus may be configured so that the control unit searches the slope having a gradient angle and a direction satisfying predetermined search conditions.

The visual inspection apparatus may be configured so that the control unit searches the slope based on a result of calculating a gradient angle and a direction of the slope from the measurement result of the three-dimensional shape.

The visual inspection apparatus may be configured so that the control unit searches a concave slope region, in which a distance between the surface of the solder and the board decreases toward the component, from the surface of the solder based on the measurement result of the three-dimensional shape and judges the quality of the state of the solder based on a result of searching the concave slope region.

In the configuration to search the concave slope region from the surface of the solder in this way, if the solder has such a defective shape that the amount of the solder is small near the component and, on the other hand, the solder rises with distance from the component, the concave slope region present in such a defective shape can be detected. Thus, even if the solder has such a defective shape, the quality of the state of the solder can be properly judged based on the result of searching the concave slope region.

Further, the visual inspection apparatus may be configured so that the control unit searches the concave slope region satisfying a predetermined search condition. By imposing the search condition to be satisfied by the concave slope region in this way, the quality of the state of the solder can be more properly judged as illustrated later.

Specifically, the visual inspection apparatus may be configured so that the control unit searches the concave slope region satisfying the search condition that an inclination direction is within a predetermined inclination angle range. Or the visual inspection apparatus may be configured so that the control unit searches the concave slope region satisfying the search condition that a gradient angle is within a predetermined gradient angle range.

The visual inspection may be configured to further comprise a setting unit that set the search condition according to a content input from a user. In such a configuration, a user can set a reference for judging the quality of the state of the solder. As a result, the quality of the state of the solder can be judged with accuracy required by the user.

Incidentally, various specific modes of determining the quality of the state of the solder based on the result of searching the concave slope region are conceivable. Thus, the visual inspection apparatus may be configured to judge that the state of the solder is poor in the case of detecting the concave slope region. However, such as when the detected concave slope region has a small area, it is not always appropriate to immediately judge that the state of the solder is poor. So the visual inspection apparatus may be configured so that the control unit judges that the state of the solder is poor in the case of detecting the concave slope region larger than a predetermined area as a result of searching the concave slope region. In such a configuration, according to the area of the concave slope region, it can be properly judged that the state of the solder is poor.

On this occasion, the quality of the state of the solder may be judged using also a result of searching a convex slope region which tends to appear on the surface of the solder having a good state. That is, the visual inspection apparatus may be configured so that the control unit searches a convex slope region, in which the distance between the surface of the solder and the board increases toward the component, from the surface of the solder based on the measurement result of the three-dimensional shape and judges the quality of the state of the solder based on a result of searching the convex slope region. As just described, the quality of the state of the solder can be more properly judged based on the result of searching the concave slope region and the result of searching the convex slope region.

More specifically, the visual inspection apparatus may be configured so that the control unit judges that the state of the solder is poor in the case of detecting no convex slope region larger than a predetermined area as a result of searching the convex slope region. In such a configuration, it can be properly judged that the state of the solder is poor.

Various specific modes are conceivable as a configuration to measure the three-dimensional shape of the surface of the solder. So the visual inspection apparatus may be configured so that the measurement unit includes an irradiator to irradiate light to the surface of the solder and a photodetector and performs a light detecting operation of detecting light irradiated from the irradiator and reflected by the surface of the solder by the photodetector and obtaining a light detection result; and the control unit calculates the three-dimensional shape based on the light detection result.

Note that, in a configuration to irradiate light from the irradiator, there may be a reflected light that is incident on the solder after being irradiated from the irradiator and reflected, for example, by the board or the component besides the light irradiated from the irradiator and directly incident on the solder. Such reflected light may reduce the calculation accuracy of the three-dimensional shape of the surface of the solder. So the visual inspection apparatus may be configured so that the control unit calculates the three-dimensional shape based on a result of searching a reflected light that is incident on the solder after being emitted from the irradiator and reflected. In such a configuration, it is possible to calculate the three-dimensional shape of the surface of the solder with high accuracy by suppressing effects of the reflected light.

The visual inspection apparatus may be configured so that the measurement unit includes a plurality of the irradiators, makes each irradiator individually light to perform the light detecting operation, and obtains the light detection result for each irradiator; and the control unit calculates the three-dimensional shape based on a result of specifying the irradiator irradiating the reflected light in the case of detecting the reflected light. In such a configuration, it is possible to calculate the three-dimensional shape of the surface of the solder with high accuracy by suppressing effects of the reflected light.

Here, various specific modes for calculating the three-dimensional shape based on the result of specifying the irradiator irradiating the reflected light are conceivable. One example is as follows. The visual inspection apparatus may be configured so that the control unit calculates a height at a position of reflection where the reflected light is incident while excluding the light detection result obtained by lighting the irradiator irradiating the reflected light whose quantity is larger than a predetermined light quantity in calculating a distance between the position of reflection and the board to calculate the three-dimensional shape. In such a configuration, it is possible to calculate the three-dimensional shape of the surface of the solder with high accuracy by suppressing effects of the reflected light.

Advantageous Effects of Invention

The slope present on the surface of the solder is searched and the quality of the state of the solder is judged based on that result. The quality of the state of the solder can be properly judged based on not a height of the solder, but the slope of the surface of the solder in this way.

BRIEF DESCRIPTION OF DRAWINGS

FIG. 9 is a diagram schematically illustrating a case where the state of the solder B joining the component to the board is good.

DETAILED DESCRIPTION

Figure 1:
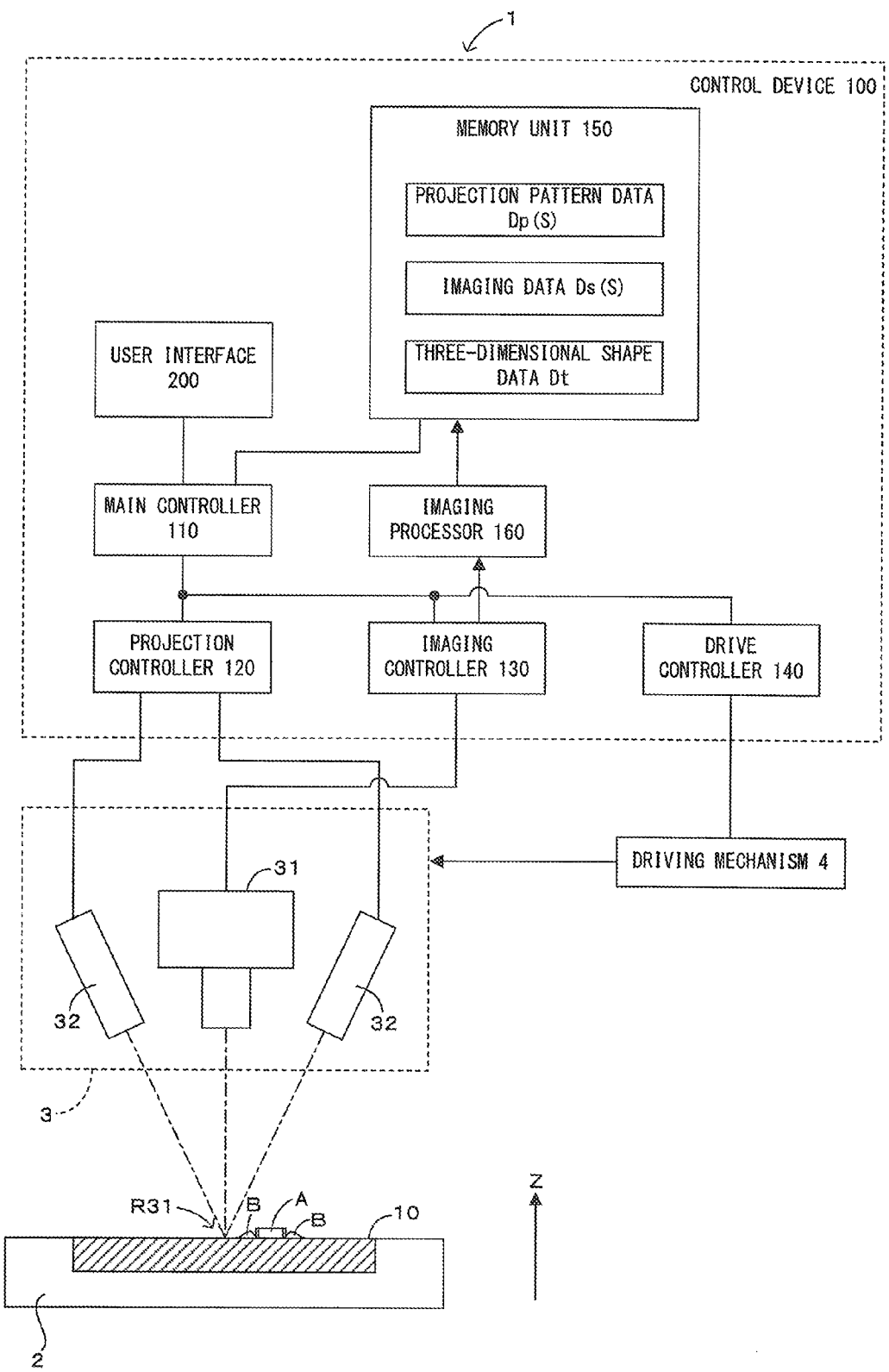
FIG. 1 is a block diagram schematically illustrating a visual inspection apparatus according to the disclosure.

FIG. 1 is a block diagram schematically illustrating a visual inspection apparatus according to the disclosure. This visual inspection apparatus 1 inspects the quality of a state of solder B joining a component (electronic component) to a board 10 (printed circuit board) by controlling a carrying conveyor 2, an inspection head 3 and a driving mechanism 4 by a control device 100.

The carrying conveyor 2 carries the board 10 along a predetermined carrying path. Specifically, the carrying conveyor 2 carries the board 10 before inspection to an inspection position in the visual inspection apparatus 1 and horizontally holds the board 10 at the inspection position. Further, when the inspection of the board 10 at the inspection position is finished, the carrying conveyor 2 carries out the board 10 after inspection to the outside of the visual inspection apparatus 1.

The inspection head 3 includes an imaging camera 31 for imaging the interior of an imaging region R31 from above, and accommodates the solder B (inspection object part) of the board 10 carried to the inspection position in the imaging region R31 and images by the imaging camera 31. For example, a CCD (Charge Coupled Device) camera can be used as such an imaging camera 31. Further, the inspection head 3 includes projectors 32 for projecting stripe pattern light (pattern light), whose light intensity distribution sinusoidally changes, to the imaging region R31. The projector 32 includes a light source such as an LED (Light Emitting Diode) and a digital micromirror device for reflecting light from the light source toward the imaging region R31. Such projectors 32 can project a plurality of types of pattern light having mutually different phases to the imaging region R1 by adjusting an angle of each micromirror of the digital micromirror devices. That is, the inspection head 3 can measure a three-dimensional shape of the solder B in the imaging region R31 by a phase-shifting method by performing imaging by the imaging camera 31 while changing the phases of the pattern light projected from the projectors 32.

Incidentally, the inspection head 3 includes eight projectors 32 (two projectors 32 are shown as representatives to simplify graphical representation in FIG. 1). The eight projectors 32 are arranged around the imaging camera 31 and circumferentially arranged at an equal interval around a vertical direction Z. Each projector 32 projects the pattern light to the imaging region R31 of the imaging camera 31 from an oblique upper side. In this way, the pattern light can be projected to the imaging region R31 from mutually different directions.

The driving mechanism 4 drives the inspection head 3 in horizontal and vertical directions by a motor while supporting the inspection head 3. By being driven by this driving mechanism 4, the inspection head 3 can move upwardly of the solder B, capture the solder B in the imaging region R31 and measure the three-dimensional shape of the solder B in the imaging region R31.

The control device 100 includes a main controller 110 comprising a CPU (Central Processing Unit) and a memory and an inspection is conducted by the main controller 110 controlling each part of the apparatus. Further, the control device 100 includes a user interface 200 comprising a display and input/output devices such as a keyboard and a mouse and a user can input a command to the control device 100 and confirm an inspection result by the control device 100 via the user interface 200. Further, the control device 100 includes a projection controller 120 for controlling the projectors 32, an imaging controller 130 for controlling the imaging camera 31 and a drive controller 140 for controlling the driving mechanism 4. When the carrying conveyor 2 carries the board 10 to the inspection position, the main controller 110 controls the driving mechanism 4 by the drive controller 140 and moves the inspection head 3 to a position above the solder B on the board 10. This causes the solder B to be accommodated in the imaging region R31 of the imaging camera 31.

Subsequently, the main controller 110 images the pattern light projected to the imaging region R31 by the imaging camera 31 while projecting the pattern light to the imaging region R31 including the solder B from the projectors 32 (pattern imaging operation). Specifically, the main controller 110 includes a memory unit 150 comprising a nonvolatile memory and reads projection pattern data Dp(S) stored in the memory unit 150. Then, the main controller 110 adjusts the angle of each micromirror of the digital micromirror devices of the projectors 32 according to the projection pattern data Dp(s) by controlling the projection controller 120 based on the projection pattern data Dp(s) read from the memory unit 150. In this way, the pattern light corresponding to the projection pattern data Dp(S) is projected to the imaging region R31. Further, the main controller 110 images the pattern light projected to the imaging region R31 by controlling the imaging controller 130. This imaging result is converted into imaging data Ds(S) in an imaging processor 160 of the main controller 110 and stored in the memory unit 150. Note that four types of pieces of the projection pattern data Dp(s) having mutually different phases are stored in the memory unit 150 (S=1, 2, 3, 4) and the pattern imaging operation is performed four times while changing the projection pattern data Dp(S). As a result, four types of pieces of the imaging data Ds(S) indicating the imaged pattern light having mutually different phases are obtained.

The main controller 110 calculates a height of the imaging region R31 for each pixel of the imaging camera 31 by the phase-shifting method from the thus obtained four types of pieces of the imaging data Ds(S). In this way, a height h (FIG. 2) of a surface of the solder B is calculated for each pixel of the imaging camera 31. Note that the height of the imaging region R31 is calculated, for example, as a distance between a point corresponding to a target pixel in the imaging region R31 and the board 10. Further, the height h of the surface of the solder B is calculated, for example, as a distance between the board 10 (or reference plane parallel to the board 10) and the surface of the solder B and, in a configuration in which the board 10 is horizontally held, calculated as a distance between the board 10 (or reference plane parallel to the board 10) and the surface of the solder B in the vertical direction Z (i.e. direction perpendicular to the board 10). In this way, three-dimensional shape data Dt including data indicating the height h of the surface of the solder B for each pixel is calculated and stored in the memory unit 150.

The main controller 110 judges the quality of a state of the solder B based on the thus obtained three-dimensional shape data Dt. Particularly, the main controller 110 judges the quality of the state of the solder B based on a result of searching a concave slope region in which the distance between the surface of the solder B and the board 10 (height h) decreases toward the component A (in other words, downslope region descending toward the component A) from the surface of the solder B.

Figure 2:
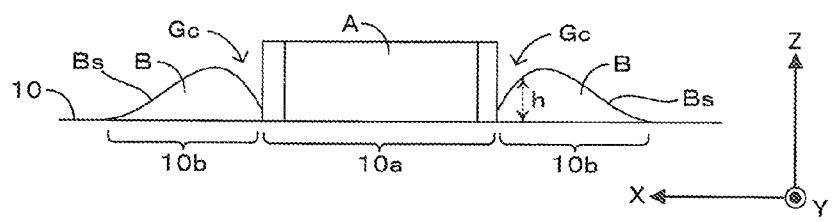
FIG. 2 is a view schematically illustrating a case where the state of the solder joining the component to the board is poor.
Figure 3:
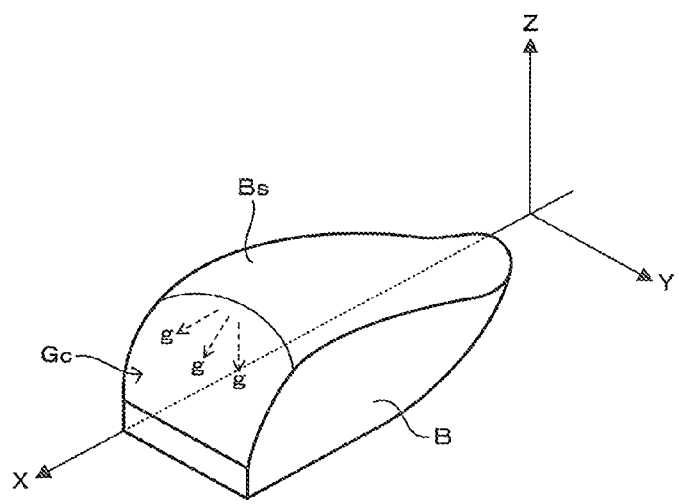
FIG. 3 is a perspective view schematically illustrating the shape of the solder arranged to the right of the component in FIG. 2.

FIG. 2 is a view schematically illustrating a case where the state of the solder joining the component to the board is poor. FIG. 3 is a perspective view schematically illustrating the shape of the solder arranged to the right of the component in FIG. 2. In this example, a component arrangement region 10a and solder arrangement regions 10b (lands) adjacent to the component arrangement region 10a are provided on a surface of the board 10. The component A arranged in the component arrangement region 10a is joined to the surface of the board 10 by the solder B attached in the solder arrangement regions 10b. Note that, in FIGS. 2 and 3 and subsequent figures, XYZ orthogonal coordinate axes with a direction, in which the component arrangement region 10a and the solder arrangement regions 10b are juxtaposed, as an X direction are shown as appropriate. For example, these XYZ orthogonal coordinate axes can be set for each solder B to be inspected, and the X direction is a positive direction from the solder B toward the component A.

In this example, the component A repels the solder B due to poor wettability of the solder B. Thus, the solder B has such a defective shape that the amount of the solder B is small near the component A and, on the other hand, the solder B rises with distance from the component A in the X direction. If such a defective shape is formed, a concave slope region Gc is formed on a surface Bs of the solder B near a boundary between the component A and the solder B.

The main controller 110 judges the quality of the solder B based on a result of searching the concave slope region Gc of the defective shape of the solder B to conduct a proper inspection compatible with such a defective surface.

Incidentally, the concave slope region Gc notably appears when the state of the solder B is poor, but it may appear even if the state of the solder B is good. Thus, in the case of immediately judging the quality of the state of the solder B based on the result of searching the concave slope region Gc, it is also possible to judge that the state of the solder B is poor although the state of the solder B is good. However, the concave slope region Gc differs in an inclination direction, a gradient angle and other tendencies between the case where the state of the solder B is good and the case where it is poor. Specifically, if the state of the solder B is poor, the concave slope region Gc having an inclination direction oriented more toward the X direction (in other words, an angle to the X direction is small) tends to notably appear and the concave slope region Gc having a steep gradient angle tends to notably appear.

Utilizing such tendencies, the main controller 110 searches the concave slope region Gc whose inclination direction and gradient angle satisfy predetermined conditions. At this time, the inclination direction and the gradient angle of the concave slope region Gc are not uniform and have a distribution. Specifically, as shown in FIG. 3, the inclination direction and the gradient angle differ depending on minute slopes g (e.g. slopes of regions corresponding to one pixel) constituting the surface Bs of the solder B. Note that, in FIG. 3, the minute slope g is represented by a broken-line arrow having an inclination direction and a gradient angle of this region.

Figure 4:
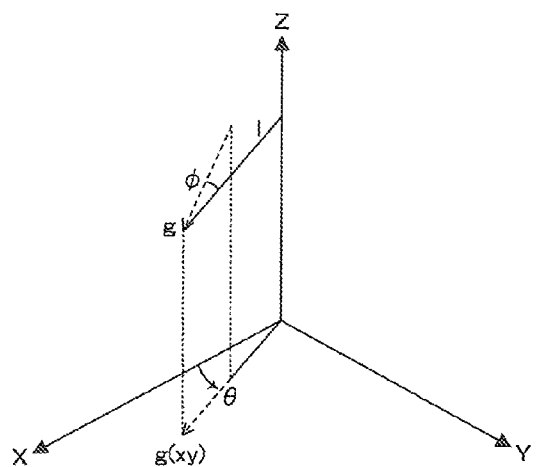
FIG. 4 is a graph showing the inclination direction and the gradient angle of the minute slope.

FIG. 4 is a graph showing the inclination direction and the gradient angle of the minute slope. In FIG. 4, the inclination direction $\theta$ and the gradient angle $\varphi$ are shown for the minute slope g. The inclination direction $\theta$ is calculated as an angle formed between a shadow g(xy) obtained by projecting the minute slope g on an XY plane and the X direction and corresponds to an azimuth angle of the minute slope g. The gradient angle $\varphi$ is calculated as an angle formed between a straight line 1 parallel to the shadow g(xy) and the minute slope g and corresponds to an elevation angle of the minute slope g.

Accordingly, the main controller 110 searches the concave slope region Gc having the minute slopes g whose inclination directions $\theta$ lie within a predetermined inclination angle range and whose gradient angles $\theta$ lie within a predetermined gradient angle range. At this time, the user can set the inclination angle range and the gradient angle range on the user interface 200.

Figure 5:
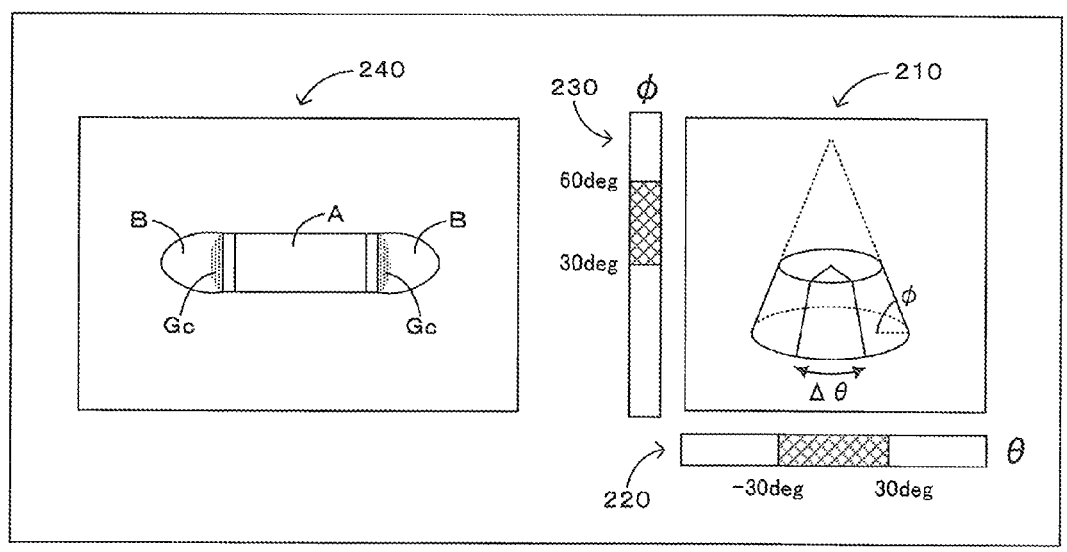
FIG. 5 is a diagram schematically illustrating the configuration of the user interface.

FIG. 5 is a diagram schematically illustrating the configuration of the user interface. The user interface 200 includes an angle setting screen 210, a $\theta$ setter 220 and a $\varphi$ setter 230. The user can change each of a minimum value $\theta$min (−30° in an example of FIG. 5) and a maximum value $\theta$max (+30° in the example of FIG. 5) of the inclination angle range by operating the $\theta$ setter 220. Similarly, the user can change each of a minimum value $\varphi$min (30° in the example of FIG. 5) and a maximum value $\varphi$max (+60° in the example of FIG. 5) of the gradient angle range by operating the $\varphi$ setter 230. On the angle setting screen 210, an image suitable to visually confirm the angles $\theta$, $\varphi$ set in this way is displayed. On the angle setting screen 210 in the example of FIG. 5, an inclination angle range $\Delta\theta$ and a representative gradient angle $\varphi$ (e.g. median value) of the gradient angle range is displayed using a conical shape. Further, the user interface 200 includes a display screen 240. On this display screen 240, the solder B having the concave slope region Gc searched therefor as an result of inspection can be, for example, displayed while the concave slope region Gc is highlighted.

Figure 6:
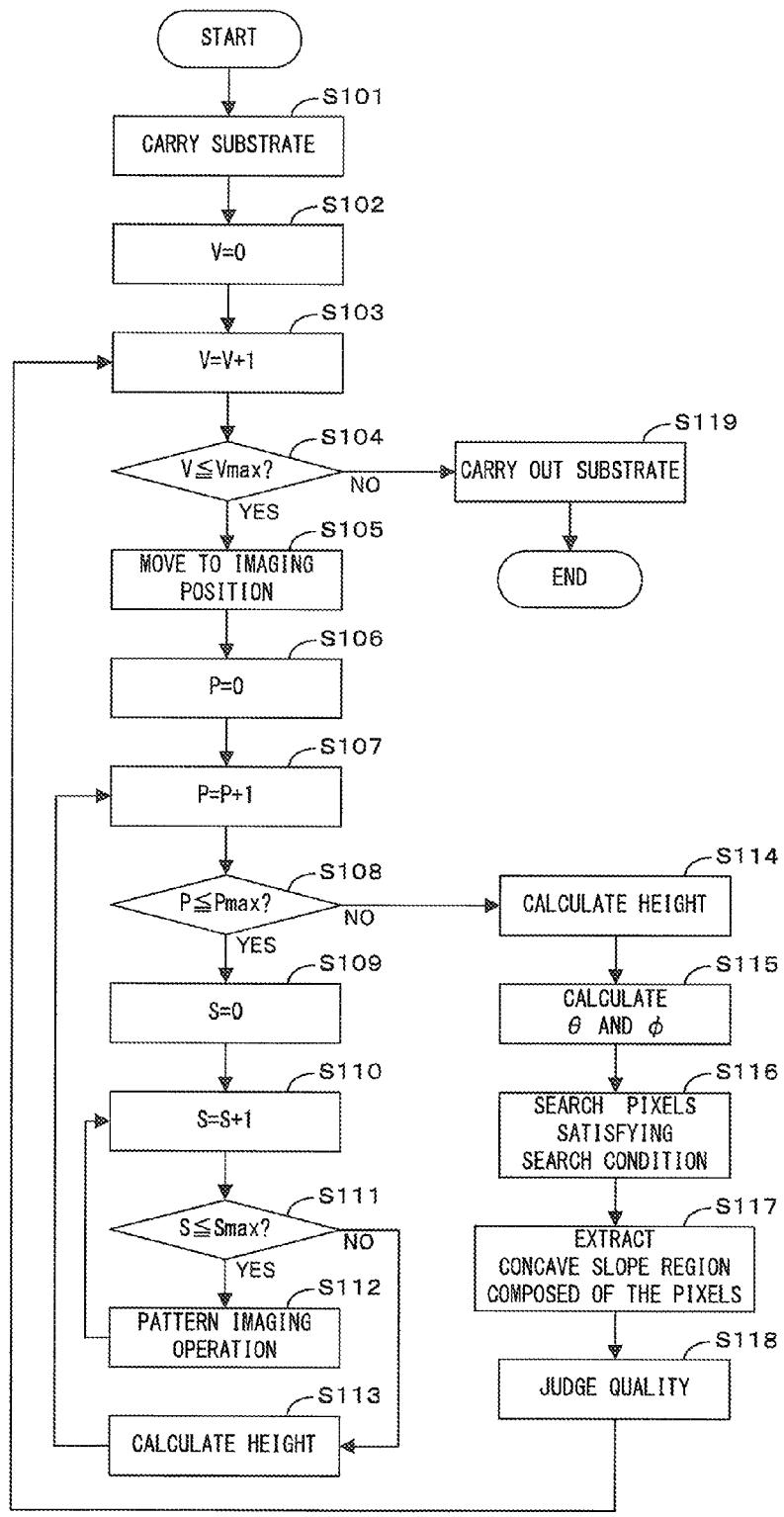
FIG. 6 is a flow chart illustrating the contents of an inspection conducted in the visual inspection apparatus.

FIG. 6 is a flow chart illustrating the contents of an inspection conducted in the visual inspection apparatus. This flow chart is performed by the main controller 110 controlling each part of the apparatus. In Step S101, the board 10 is carried to the inspection position. Subsequently, after a variable V indicating an imaging position (view) of the imaging camera 31 is set to zero in Step S102, the variable V is incremented in Step S103. Then, in Step S104, it is judged whether or not the variable V is less-than-or-equal-to Vmax. That is, a plurality of (Vmax) imaging positions are set for the board 10 and the operations of subsequent Steps S105 to S118 are performed at each imaging position while moving the imaging camera 31 successively to the plurality of imaging positions by incrementing the variable V until the variable V reaches Vmax. Specifically, if it is judged in Step S104 that the variable V is less-than-or-equal-to Vmax (i.e. "YES"), an advance is made to Step S105 in which the imaging camera 31 is moved to the imaging position indicated by the variable V. In this way, the solder B and the periphery (board 10, component A) of the solder B corresponding to the variable V are accommodated in the irradiation region R31.

Subsequently, after a variable P identifying the eight projectors 32 is set to zero in Step S106, the variable P is incremented in Step S107. Then, in Step S108, it is judged whether or not the variable P is less-than-or-equal-to Pmax (=8). That is, the operations of subsequent Steps S109 to S112 are performed while switching the projector 32 for projecting the pattern light one by one among the eight projectors 32 by incrementing the variable P until the variable P reaches Pmax.

After a variable S identifying four pieces of projection pattern data Dp(S) indicating pattern light having mutually different phases is set to zero in Step S109, the variable S is incremented in Step S110. Then, in Step S111, it is judged whether or not the variable S is less-than-or-equal-to Smax (=4). That is, the operation of subsequent Step S112 is performed while switching the phase of the pattern light to be projected among four patterns by incrementing the variable S until the variable S reaches Smax.

Specifically, the pattern imaging operation of imaging the pattern light projected to the imaging region R31 by the imaging camera 31 while projecting the pattern light to the imaging region R31 from the projectors 32 is performed for each of four types of the pattern light to obtain four types of pieces of imaging data Ds(S). When the obtainment of the four types of pieces of imaging data Ds(S) is finished (judgment of "NO" in Step S111), an advance is made to Step S113 to calculate the three-dimensional shape data Dt of the imaging region R1 including the solder B by the phase-shifting method and a return is made to Step S107. In this way, Steps S108 to S113 are repeated while incrementing the variable P, thereby being able to obtain eight pieces of three-dimensional shape data Dt when the pattern light is projected from the mutually different projectors 32. Incidentally, the three-dimensional shape data Dt obtained in this way includes data indicating the three-dimensional shape of the solder B and that indicating the three-dimensional shape of the periphery (board 10, component A, etc.) of the solder B.

After the obtainment of the three-dimensional shape data Dt for all of the eight projectors 32 is finished (judgment of "NO" in Step S108), an advance is made to Step S114. In this Step S114, the three-dimensional shape of the imaging region R1 including the solder B is finally determined out of the eight pieces of three-dimensional shape data Dt. Specifically, the three-dimensional shape of the imaging region R31 may be determined by averaging the heights h indicated by the eight pieces of three-dimensional shape data Dt for each pixel or the three-dimensional shape of the imaging region R31 may be determined by averaging the heights h left after deleting outliers out of the heights h indicated by the eight three-dimensional shape data Dt for each pixel.

When the three-dimensional shape data Dt indicating the three-dimensional shape of the imaging region R31 including the solder B is finally determined in Step S114, the angles θ, φ are calculated for each pixel in Step S115. For example, the inclination θ and the gradient angle φ of a tangent plane or a plane approximate to the tangent plane to a minute region (region corresponding to a calculation target pixel) constituting the surface of the imaging region R31 (including the surface Bs of the solder B) are calculated. An example of a calculation method is as follows. First, a plane extending along the heights indicated by the calculation target pixel and four pixels adjacent to the calculation target pixel on four sides is approximately calculated. For example, a least square method or the like can be used as a method of plane approximation. The inclination direction θ and the gradient angle φ of this plane may be calculated as the inclination direction θ and the gradient angle φ of the calculation target pixel. A specific example is as follows. When an equation of the plane is:

$$Z=\alpha \times x + \beta \times y + \gamma,$$

the angles θ, φ can be calculated by the following equations.

$$\theta[rad]=\arctan(\beta/\alpha) \text{ when } \alpha>0,$$

$$\theta[rad]=\arctan(\beta/\alpha)+\pi \text{ when } \alpha<0,$$

$$\varphi=\arctan(\sqrt{\alpha^2+\beta^2})$$ [Equations 1]

When the angles θ, φ are calculated for each pixel (including each pixel of the surface Bs of the solder B) corresponding to the imaging region R31 in Step S115, Steps S116 and S117 are performed. That is, the pixels having the angles θ, φ within the ranges of search conditions (θmin≤θ≤θmax, φmin≤φ≤φmax) set by the user are searched (Step S116) and the concave slope region Gc constructed from the pixels satisfying the search conditions is extracted (Step S117). In Step S118, the quality of the solder B is judged based on the result of searching the concave slope region Gc in this way. Specifically, if the concave slope region Gc larger than a predetermined area (threshold area for concave slope) is detected, the state of the solder B having this concave slope region Gc on the surface is judged to be defective.

When the quality judgment in Step S118 is completed, a return is made to Step S103. Then, the quality of the solder B is judged by performing the operations of subsequent Steps S105 to S118 for each imaging position while moving the imaging camera 31 successively to the plurality of imaging positions by incrementing the variable V until the variable V reaches Vmax. When the variable V reaches Vmax and the quality judgment of the solder B is completed at all the imaging positions, the board 10 is carried out (Step S119) and the flow chart of FIG. 6 is finished.

As described above, in this embodiment configured as just described, the slope (concave slope region Gc) present on the surface Bs of the solder B is searched and the quality of the state of the solder B is judged based on that search result.

The quality of the state of the solder B can be properly judged based on not the height of the solder B, but the slope (concave slope region Gc) of the surface Bs of the solder B.

Further, in this embodiment, the concave slope region Gc in which the distance (height h) between the surface B s of the solder B and the board 10 decreases toward the component A is searched from the surface Bs of the solder B. In such a configuration, if the solder B has such a defective shape that the amount of the solder B is small near the component A and, on the other hand, the solder B rises with distance from the component A, the concave slope region Gc present in such a defective surface can be searched. Thus, even if the solder B has such a defective surface, the quality of the state of the solder B can be properly judged based on the result of searching the concave slope region Gc.

Incidentally, the concave slope region Gc as described above notably appears when the state of the solder B is poor. However, the concave slope region Gc may appear even if the state of the solder B is good. Thus, in the case of judging the quality of the state of the solder B based on the result of searching the concave slope region Gc, it is also possible to judge that the state of the solder B is poor although the state of the solder B is good. However, the concave slope region Gc differs in the inclination direction θ, the gradient angle φ and other tendencies between the case where the state of the solder B is good and the case where it is poor as described above. Accordingly, in this embodiment, the control device 100 searches the concave slope region Gc satisfying the predetermined search conditions (inclination angle range, gradient angle range). By imposing the search conditions to be satisfied by the concave slope region Gc in this way, it can be suppressed to judge that the state of the solder B is poor although the state of the solder B is good.

Further, the user interface 200 for setting the search conditions according to the contents input from the user is provided in this embodiment. In such a configuration, the user can set a reference for judging the quality of the state of the solder B. As a result, the quality of the state of the solder B can be judged with accuracy required by the user.

Incidentally, various specific modes of determining the quality of the state of the solder B based on the result of searching the concave slope region Gc are conceivable. Thus, the state of the solder B may be judged to be poor in the case of detecting the concave slope region Gc. However, such as when the detected concave slope region Gc has a small area, it is not always appropriate to immediately judge that the state of the solder B is poor. Accordingly, the control device 100 of this embodiment judges that the state of the solder B is poor in the case of detecting a concave slope region Gc larger than a predetermined area (threshold area for concave slope) as a result of searching the concave slope region Gc. In such a configuration, according to the area of the concave slope region Gc, it can be properly judged that the state of the solder B is poor.

At this time, the value of the threshold area for concave slope may be set by the user using the user interface 200. This enables the quality of the state of the solder B to be judged with accuracy required by the user.

As just described, in this embodiment, the visual inspection apparatus corresponds to an example of a "visual inspection apparatus" of the disclosure, the inspection head 3 and the control device 100 cooperate and function as an example of a "measurement unit", the control device 100 corresponds to an example of a "control unit" of the disclosure, the user interface 200 corresponds to an example of a "setting unit" of the disclosure, and the concave slope region Gc corresponds to an example of a "concave slope region" of the disclosure.

Figure 7:
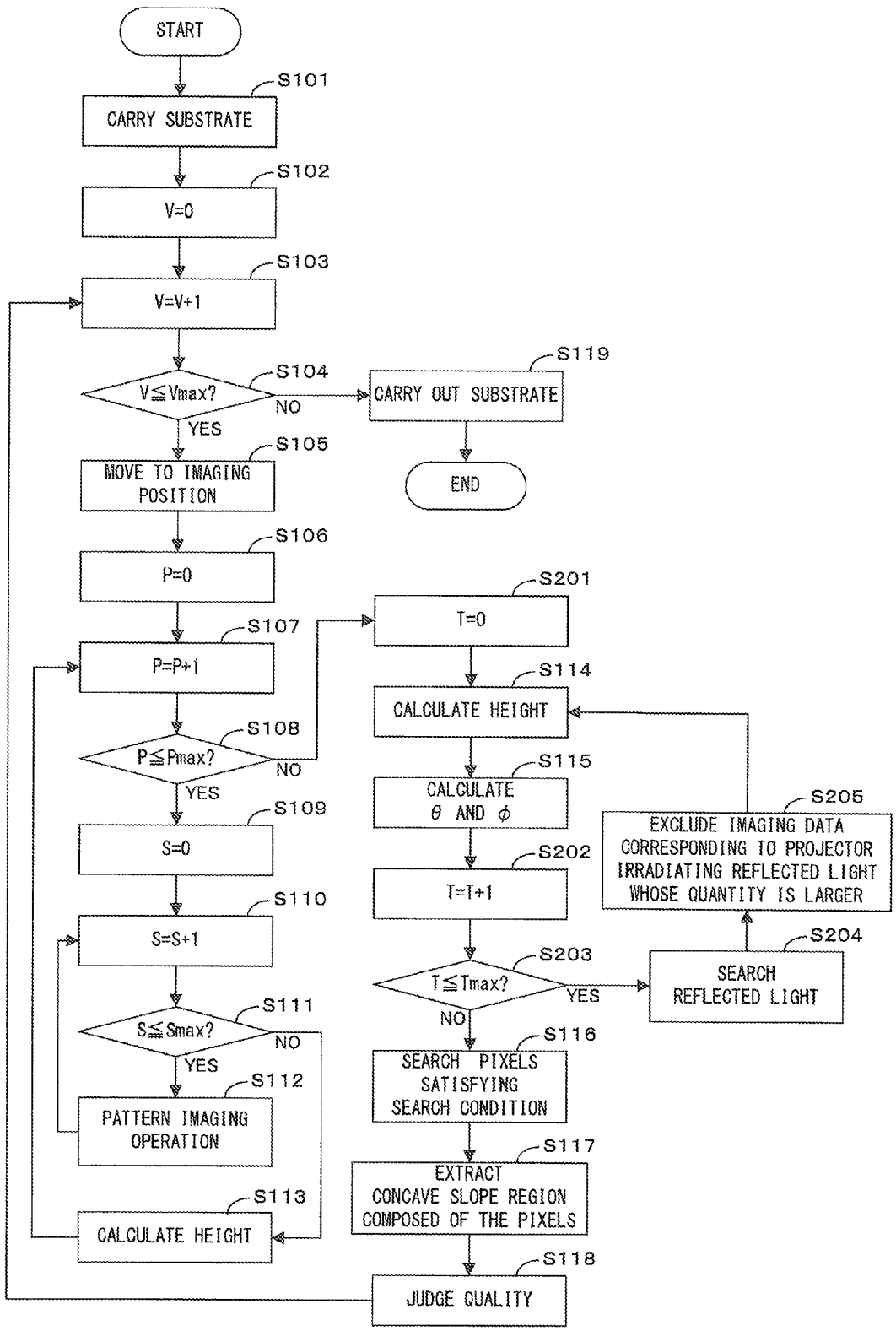
FIG. 7 is a flow chart showing a modification of the contents of the inspection conducted in the visual inspection apparatus.

Note that the disclosure is not limited to the above embodiment and various changes other than the aforementioned ones can be made without departing from the gist of the disclosure. For example, the control device 100 may be configured to perform a flow chart shown in FIG. 7. Here, FIG. 7 is a flow chart showing a modification of the contents of the inspection conducted in the visual inspection apparatus. The following description is centered on points of difference from the above embodiment and common points are denoted by corresponding reference signs and not described.

As described above, the visual inspection apparatus 1 is provided with the plurality of projectors 32 (irradiators) for irradiating pattern light to the surface Bs of the solder B from mutually different directions and the imaging camera 31 (photodetector). The pattern light projected to the solder B from the projectors 32 is imaged by the imaging camera 31 and the pattern imaging operation (light detecting operation) of obtaining the imaging data Ds(S) is performed by lighting the plurality of projectors 32 individually.

In such a configuration, a reflected light that is incident on the solder B after being irradiated from the projectors 32 and reflected, for example, by the board 10 or the component A can be present besides the light irradiated from the projectors 32 and directly incident on the solder B. Such reflected light may reduce the calculation accuracy of the three-dimensional shape of the surface Bs of the solder B. In contrast, in the flow chart of FIG. 7, the three-dimensional shape of the surface Bs of the solder B is calculated while effects of the reflected light are corrected.

Specifically, if "NO" is judged in Step S108, a variable T is set to zero in Step S201. Such a variable T is set to perform a loop operation of Steps S114, S115, S202 to S205 for correcting the effects of the reflected light until the variable T reaches Tmax. Subsequently, as in the above embodiment, the three-dimensional shape of the imaging region R31 including the surface Bs of the solder B is determined in Step S114 and the angles θ, φ are calculated in Step S115. Subsequently, the variable T is incremented in Step S202 and it is judged in Step S203 whether or not the variable T is less-than-or-equal-to Tmax. If it is judged in Step S203 that the variable T is less-than-or-equal-to Tmax, an advance is made to Step S204.

Figure 8:
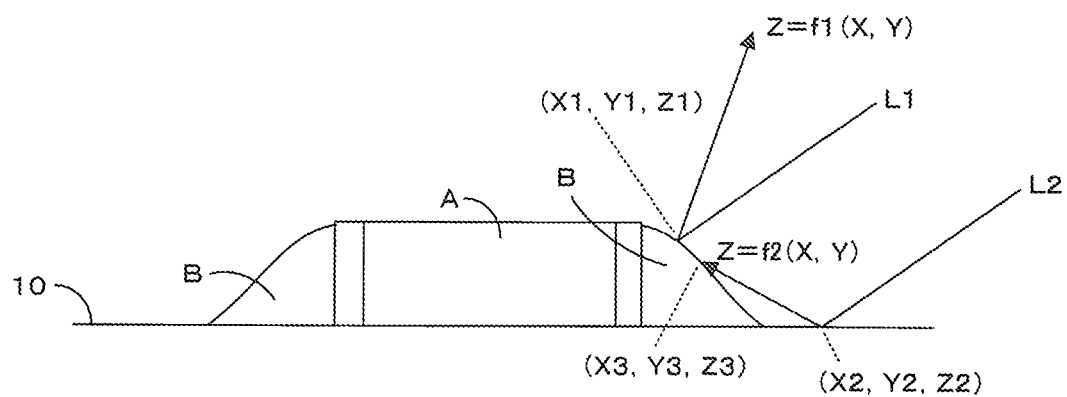
FIG. 8 is a diagram showing an example of a reflected light searching method.

In Step S204, the reflected light is searched. FIG. 8 is a diagram showing an example of a reflected light searching method. In FIG. 8, rays of light L1, L2 emitted from the same projector 32 are illustrated. The ray of light L1 is directly incident on the solder B, whereas the ray of light L2 is incident on the solder B after being reflected by the board 10 and becomes reflected light. Incidentally, any of pieces of data (X1, Y1, Z1), (X2, Y2, Z2) and (X3, Y3, Z3) is a result of calculating a height Z at each position (X, Y) in Step S114.

In searching the reflected light, an equation indicating a locus of light reflected at each point on the solder B, the board 10 and the component A is obtained based on the three-dimensional shape (X, Y, Z) of the imaging region R31 calculated in Step S114, the angles θ, φ and the like. For example, in FIG. 8, the following equation is obtained as an equation indicating a locus of the ray of light L1 reflected at a point (X1, Y1, Z1) on the solder B.

$$Z=f1(X,Y)  \quad \text{Equation 1}$$

The following equation is obtained as an equation indicating a locus of the ray of light L2 reflected at a point (X2, Y2, Z2) on the board 10.

$$Z=f2(X,Y) \quad \text{Equation 2}$$

Since the locus of the ray of light expressed by Equation 1 does not match with the surface of the solder B other than at the point (X1, Y1, Z1), there is only one piece of data (X1, Y1, Z1) satisfying Equation 1 out of the data indicating the three-dimensional shape of the surface Bs of the solder B. On the other hand, the locus of the ray of light expressed by Equation 2 matches with the surface Bs of the solder B at a point (X3, Y3, Z3) besides at the point (X2, Y2, Z2). Thus, not only data (X2, Y2, Z2), but also data (X3, Y3, Z3) satisfy Equation 2. As just described, in the occurrence of reflection, two pieces (or more) of data satisfy the equation indicating the reflection light out of the data obtained in Step S114. In other words, if the equation indicating the locus of the reflection light at each point is obtained and two or more pieces of data satisfying the same equation are found out of the data indicating the three-dimensional shape of the surface Bs of the solder B, the light corresponding to this equation can be judged to be reflected light.

Further, in Step S204, the projector 32 emitting the reflected light is specified and an XY position corresponding to an incident position of the reflected light on the surface Bs of the solder B (i.e. pixel position) is specified when the reflected light is detected. Then, the projector 32 specified in this way and the XY position where the reflected light is incident are associated.

In Step S205, the quantity of the reflected light incident on the position of the surface Bs of the solder B corresponding to each pixel is estimated. At this time, if there are a plurality of rays of the reflected light incident on the same XY position, the quantity of each ray of the reflected light is calculated. Then, a process of excluding the imaging data Ds(S) obtained by lighting the projector 32 irradiating the reflected light whose quantity is larger than a predetermined light quantity (threshold light quantity) is performed for each XY position.

In subsequent Step S114, the three-dimensional shape of the surface Bs of the solder B is calculated again based on the imaging data Ds(S) from which the data affected by the reflected light is excluded in this way. This causes the three-dimensional shape data Dt to be obtained in Step S114 after excluding the imaging data Ds(S) obtained by lighting the projector 32 irradiating the reflected light whose quantity is larger than the predetermined light quantity.

The three-dimensional shape calculated first in Step S114 is affected by the reflected light and there is a possibility that the accuracy thereof is not necessarily high. Thus, the reflected light searched based on such a three-dimensional shape may include an error. Such an error in the result of searching the reflected light may lead to an erroneous judgment of judging that no reflected light is incident although reflected light is actually incident. However, the above loop operation can improve the calculation accuracy of the three-dimensional shape even in the case of such an erroneous judgment. Specifically, the result is neither improved nor deteriorated at a position where no reflected light is judged to be incident although reflected light is actually incident. On the other hand, the result is improved if a position where reflected light is actually incident can be correctly judged. Thus, the accuracy of the three-dimensional shape can be basically improved in the case of performing the above loop operation.

Further, the accuracy of the three-dimensional shape data Dt can be basically more improved with an increase in the number of times (i.e. Tmax) of the loop operation. Accordingly, if the user interface 200 is configured such that the user can set Tmax, the three-dimensional shape data Dt can be obtained with accuracy required by the user. When the loop operation of a predetermined number of times Tmax is finished, the operations in Step S116 and subsequent Steps are performed as in the above embodiment.

As described above, in the modification of FIG. 7, the control device 100 calculates the three-dimensional shape of the surface Bs of the solder B based on the result of searching the reflected light incident on the solder B after being emitted from the projectors 32 and reflected. In such a configuration, it is possible to calculate the three-dimensional shape of the surface Bs of the solder B with high accuracy by suppressing the effects of the reflected light.

Further, the control device 100 calculates the three-dimensional shape based on the result of specifying the projector 32 irradiating reflected light when the reflected light is detected. In such a configuration, it is possible to calculate the three-dimensional shape of the surface Bs of the solder B with high accuracy by suppressing the effects of the reflected light.

Specifically, in calculating the distance (height) between the position of reflection where the reflected light is incident and the board 10 to calculate the three-dimensional shape, the control device 100 calculates the height at the position of reflection while excluding the imaging data Ds(S) (light detection result) obtained by lighting the projector 32 irradiating the reflected light whose quantity is larger than the predetermined light quantity. In such a configuration, it is possible to calculate the three-dimensional shape of the surface Bs of the solder B with high accuracy by suppressing the effects of the reflected light.

Note that a specific mode for calculating a three-dimensional shape based on a result of specifying an irradiator irradiating reflected light is not limited to a mode of excluding the imaging data Ds(S) corresponding to the projector 32 irradiating the reflected light whose quantity is larger than the predetermined light quantity as described above. That is, the three-dimensional shape may be calculated using the imaging data Ds(S) corresponding to the projector 32 irradiating a minimum quantity of reflected light, the three-dimensional shape may be calculated using an average value of the imaging data Ds(S) corresponding to a predetermined number (e.g. two) of the projectors 32 from the one irradiating a smallest quantity of reflected light or the three-dimensional shape may be calculated using a median value of the imaging data Ds(S) excluding the imaging data Ds(S) corresponding to a predetermined number (e.g. two) of the projectors 32 from the one irradiating a largest quantity of reflected light.

In the above embodiment, the quality of the solder B is judged based on the result of searching the concave slope region Gc formed on the solder B having a poor state. However, the quality of the solder B is judged based on the result of searching a convex slope region formed on the solder B having a good state. FIG. 9 is a diagram schematically illustrating a case where the state of the solder B joining the component to the board is good. In this example, the solder B fits to the component A due to good wettability thereof. Thus, the solder B has such a shape that the amount of the solder B decreases with distance from the component A in the X direction from an end of the component A. The surface Bs of such solder B has a convex slope region Gv in which the distance (height h) between the surface Bs of the solder B and the board 10 increases toward the component A (i.e. upslope region ascending toward the component).

Accordingly, the embodiment shown in FIG. 6 or 7 may be modified such that the quality of the state of the solder B is judged using also the result of searching the convex slope region Gv that tends to appear on the surface Bs of the solder B having a good state. Specifically, a Step of searching the convex slope region Gv from the surface Bs of the solder B based on the three-dimensional shape data Dt is added between Steps S117 and S118. On this occasion, as in the case of searching the concave slope region Gc, it is possible to adopt a configuration of searching the convex slope region Gv in which the angles $\theta$, $\varphi$ satisfy predetermined search conditions. Further, it is also possible to adopt a configuration of enabling the user to set the angles $\theta$, $\varphi$ indicating the search conditions of the convex slope region Gv on the user interface 200. If the convex slope region Gv larger than a predetermined area (convex slope threshold area) cannot be searched in the added Step, the state of the solder B is judged to be poor in the quality judgment in Step S118.

In such a configuration, the quality of the state of the solder B can be more properly judged based on the result of searching the concave slope region Gc and the result of searching the convex slope region Gv. Particularly, the state of the solder B is judged to be poor if no convex slope region Gv larger than the predetermined area is detected in the case of searching the convex slope region Gv. Thus, it can be properly judged that the state of the solder B is poor when the convex slope region Gv supposed to be present on the surface Bs of the solder B having a good state is not present over a sufficient area.

On this occasion, the value of the convex slope threshold value may be set by the user using the user interface 200. This enables the quality of the state of the solder B to be judged with accuracy required by the user.

Further, the quality of the state of the solder B may be judged based on the result of searching only the convex slope region Gv without searching the concave slope region Gc. Also in such a configuration, a slope (convex slope region Gv) present on the surface Bs of the solder B is searched and the quality of the state of the solder B is judged based on that result. The quality of the state of the solder B can be properly judged based on not the height of the solder B, but the slope (convex slope region Gv) of the surface Bs of the solder B as just described.

Further, a specific technique for calculating the three-dimensional shape of the solder B is not limited to the phase-shifting method described above, and various other techniques such as the one using a stereo camera may be adopted.

Further, the search conditions in searching the concave slope region Gc or the convex slope region Gv are also not limited to the above contents and can be appropriately changed.

Further, how to set the coordinate axes and how to set the angles $\theta$, $\varphi$ are also not limited to the above examples and can be appropriately changed.

The invention claimed is:

1. A visual inspection apparatus, comprising:
    a measurement unit that measures a three-dimensional shape of a surface of solder joining a component to a board; and
    a control unit that searches a first slope region, in which a distance between the surface of the solder and the board decreases toward the component, on the surface of the solder based on the measurement result of the three-dimensional shape and judges that the state of the solder is poor in the case of detecting the first slope region larger than a predetermined area based on a result of searching the first slope region.

2. The visual inspection apparatus according to claim 1, wherein the control unit searches the first slope region satisfying a search condition that an inclination direction is within a predetermined inclination angle range.

3. The visual inspection apparatus according to claim 1, wherein the control unit searches the first slope region satisfying a search condition that a gradient angle is within a predetermined gradient angle range.

4. The visual inspection apparatus according to claim 1, further comprising a setting unit that sets the search condition of the first slope region according to a content input from a user.

5. The visual inspection apparatus according to claim 1, wherein the control unit searches a second slope region, in which the distance between the surface of the solder and the board increases toward the component, from the surface of the solder based on the measurement result of the three-dimensional shape and judges that the state of the solder is poor in the case of detecting no second slope region larger than a predetermined area based on a result of searching the second slope region.

6. The visual inspection apparatus according to claim 1, wherein:
the measurement unit includes an irradiator to irradiate light to the surface of the solder and a photodetector and performs a light detecting operation of detecting light irradiated from the irradiator and reflected by the surface of the solder by the photodetector and obtaining a light detection result; and
the control unit calculates the three-dimensional shape based on the light detection result.

7. The visual inspection apparatus according to claim 6, wherein the control unit calculates the three-dimensional shape based on a result of searching a reflected light that is incident on the solder after being emitted from the irradiator and reflected.

8. The visual inspection apparatus according to claim 7, wherein:
the measurement unit includes a plurality of the irradiators, makes each irradiator individually light to perform the light detecting operation, and obtains the light detection result for each irradiator; and
the control unit calculates the three-dimensional shape based on a result of specifying the irradiator irradiating the reflected light in the case of detecting the reflected light.

9. The visual inspection apparatus according to claim 8, wherein the control unit calculates a height at a position of reflection where the reflected light is incident while excluding the light detection result obtained by lighting the irradiator irradiating the reflected light whose light quantity is larger than a predetermined light quantity in calculating a distance between the position of reflection and the board to calculate the three-dimensional shape.

10. A visual inspection method, comprising:
measuring a three-dimensional shape of a surface of solder joining a component to a board;
searching a slope region, in which a distance between the surface of the solder and the board decreases toward the component, on the surface of the solder based on the measurement result of the three-dimensional shape; and
judging that a state of the solder is poor in the case of detecting the slope region larger than a predetermined area based on a result of searching the slope region.

* * * * *